(12) United States Patent
Jung et al.

(10) Patent No.: US 10,384,081 B2
(45) Date of Patent: Aug. 20, 2019

(54) RESPIRATORY GATING SYSTEM FOR PATIENT USING NATURAL BREATHING METHOD DURING RADIATION THERAPY, AND METHOD FOR EMITTING RADIATION THEREBY

(71) Applicant: THE CATHOLIC UNIVERSITY OF KOREA INDUSTRY-ACADEMIC COOPERATION FOUNDATION, Seoul (KR)

(72) Inventors: Joo Young Jung, Seoul (KR); Do Kun Yoon, Gyeonggi-do (KR); Tae Suk Suh, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 292 days.

(21) Appl. No.: 15/304,529

(22) PCT Filed: Jul. 1, 2014

(86) PCT No.: PCT/KR2014/005866
§ 371 (c)(1),
(2) Date: Oct. 16, 2016

(87) PCT Pub. No.: WO2015/160036
PCT Pub. Date: Oct. 22, 2015

(65) Prior Publication Data
US 2017/0252576 A1  Sep. 7, 2017

(30) Foreign Application Priority Data

Apr. 16, 2014 (KR) .................. 10-2014-0045432

(51) Int. Cl.
*A61N 5/10* (2006.01)
*A61B 5/113* (2006.01)
(Continued)

(52) U.S. Cl.
CPC .......... *A61N 5/1037* (2013.01); *A61B 5/0071* (2013.01); *A61B 5/055* (2013.01);
(Continued)

(58) Field of Classification Search
CPC .. A61N 5/1037; A61N 5/1068; A61N 5/1039; A61B 5/113; A61B 6/541;
(Continued)

(56) References Cited

U.S. PATENT DOCUMENTS

2007/0244386 A1  10/2007  Steckner et al.
2008/0077038 A1*  3/2008  McDonough .......... A61B 5/055
                                                            600/538
(Continued)

FOREIGN PATENT DOCUMENTS

KR         10-0943180 B1      2/2010

*Primary Examiner* — Kaylee R Wilson
(74) *Attorney, Agent, or Firm* — Huffman Law Group, PC

(57) ABSTRACT

A respiratory gating system is disclosed that varies the orientation of a radiation emitting device according to a patient's natural breathing. A breathing respirator is provided that allows the patient's respiration amount to be measured. External markers are adhered to triangulation points around a radiation target region, such as a heart, of the patient. An image diagnosis device images the target region. A computed tomography device reveals movements of the target region caused by the respiration. Triangulations and polynomial approximations are used to estimate the trajectory of the target region in real time. Position coordinates derived from the estimated trajectory are transmitted to the radiation emitting device. The system increases the accuracy and stability of the entire radiation therapy result.

3 Claims, 2 Drawing Sheets

(51) Int. Cl.
*A61B 90/00* (2016.01)
*A61B 5/00* (2006.01)
*A61B 5/055* (2006.01)
*A61B 5/08* (2006.01)
*A61B 6/03* (2006.01)
*A61B 6/00* (2006.01)

(52) U.S. Cl.
CPC ............... *A61B 5/08* (2013.01); *A61B 5/113* (2013.01); *A61B 6/032* (2013.01); *A61B 6/541* (2013.01); *A61B 90/39* (2016.02); *A61N 5/1039* (2013.01); *A61N 5/1068* (2013.01)

(58) Field of Classification Search
CPC ......... A61B 6/032; A61B 5/08; A61B 5/0071; A61B 90/39; A61B 5/055
See application file for complete search history.

(56) References Cited

U.S. PATENT DOCUMENTS

| | | |
|---|---|---|
| 2012/0106704 A1 | 5/2012 | Maurer, Jr. et al. |
| 2013/0165770 A1 | 6/2013 | Li et al. |
| 2014/0012061 A1 | 1/2014 | Song et al. |

\* cited by examiner

[Fig. 1]
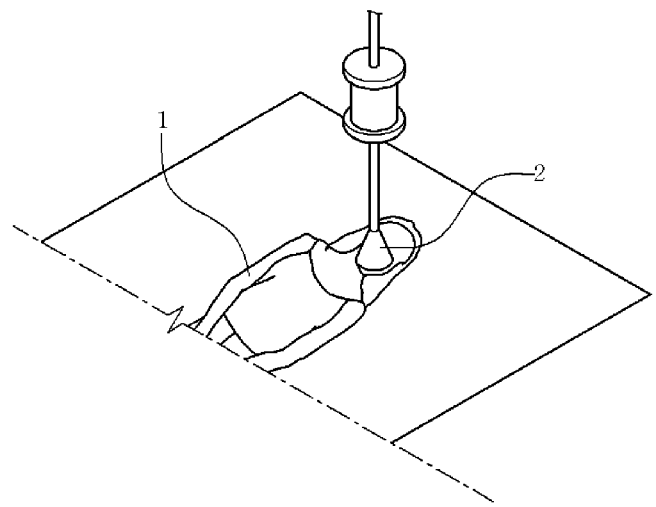
[Fig. 2]
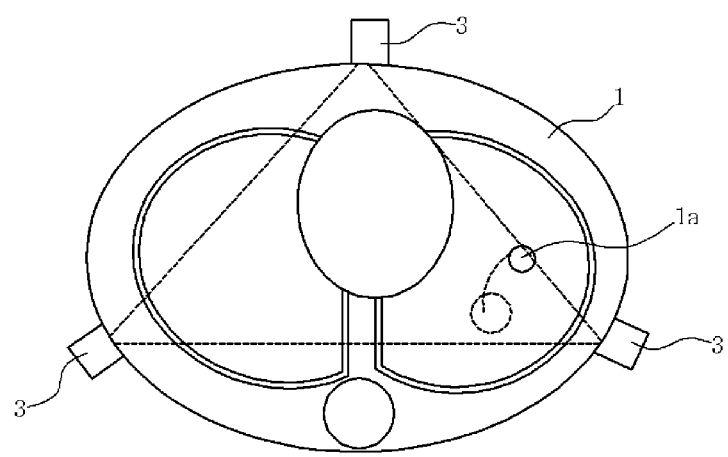

[Fig. 3]
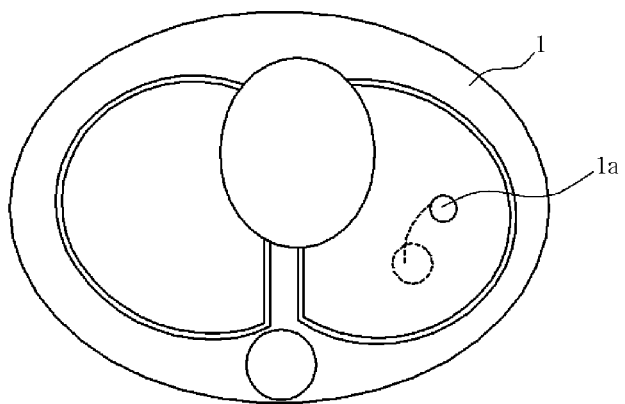
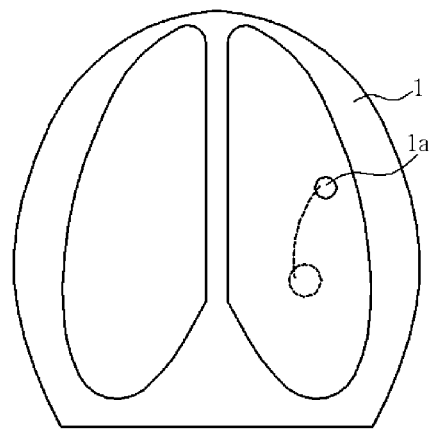

(12)  US 10,384,081 B2

RESPIRATORY GATING SYSTEM FOR PATIENT USING NATURAL BREATHING METHOD DURING RADIATION THERAPY, AND METHOD FOR EMITTING RADIATION THEREBY

TECHNICAL FIELD

The present invention relates generally to a respiratory gating system for a patient using a natural breathing method during radiation therapy and a method for emitting radiation thereby. More particularly, the present invention relates to a respiratory gating system that continually re-orients a radiation emitting device based upon tracked movements of a subject (for example, a heart) that is the target or targeted region of a radiation treatment.

BACKGROUND ART

According to a recent trend of radiation therapy, in order to check an accurate position of a subject on which a treatment is to be carried out, such as a tumor, an image guided radiation therapy (IGRT) or respiratory gated radiation therapy (RGRT) technique is used. According to the IGRT, whenever the radiation therapy is performed, an image of a subject on which treatment is to be carried out, such as a tumor of the patient, is obtained using computed tomography (CT) equipment immediately before the radiation therapy. When a therapy plan is built, the obtained image is compared to re-adjust a position where the radiation is emitted, thereby securing accuracy of the therapy. Further, according to the RGRT, a real-time position management (RPM) system is used to track a position of a subject on which treatment is to be carried out, such as a tumor, in a chest or an abdomen, according to a respiration cycle of a patient and the radiation is emitted according to the movement of the tracked position.

The method for tracking a position of a subject on which treatment is to be carried out, such as a tumor, is mainly classified into two methods: The first method is a method of tracking a position by implanting a fiducial marker (or a gold marker) in a target. The first method has an advantage in that a movement displacement of the target is accurately checked, but also has a disadvantage in that the method is invasive and the target needs to be removed after performing the therapy. The second method is a method for tracking a position using an external marker. This method is non-invasive and may secure accuracy of target localization. However, in the related art, only one external marker is provided, which may lower accuracy of tracking a position.

According to Patent Document 1 (Korean Registered Patent No. 10-0943180), a biological signal is stabilized using training and relaxation response is provided to perform bio feedback. In the above-mentioned technologies, even though high tech equipment is used to correct the movement according to respiration of a patient, a cost therefor and training for every patient are uncertain. Further, a stability of a patient which has difficulty in breathing is lowered, so that a treatment time is increased. Specifically, a recent radiation technique transmits high dose intensity at once at a short treatment time so that movement of the patient, that is, a respiration amount needs to be indispensably considered.

DISCLOSURE

Technical Problem

The present invention has been made in an effort to provide a respiratory grating system for a patient using a natural breathing method during radiation therapy which tracks the position of the subject on which treatment is to be carried out, such as a tumor, which is a target, by collecting and processing inhalation and exhalation amounts of the breathing, that is, the respiration amount in real time while maintaining natural breathing of the patient during radiation therapy, thereby removing uncertainty of a bio feedback of the related art. The respiratory grating system includes a breathing respirator which is worn by the patient, three external markers and an image diagnosis device which measures and photographs the change in position of the subject on which treatment is to be carried out according to the depth and the amount of the respiration which is transmitted through the breathing respirator, and a computer program which tracks a trajectory according to the measured change in position of the subject on which treatment is to be carried out to convert the trajectory as a vector and calculates, as position coordinates, the vector using a triangulation method and dual polynomial equations and transmits the position coordinates to radiation therapy equipment.

The present invention has been made in an effort to further provide a method for emitting radiation by a respiratory gating system for a patient using a natural breathing method during radiation therapy.

Technical Solution

According to an aspect of the present invention, there is provided a respiratory gating system for a patient using a natural breathing method during radiation therapy allows radiation to be emitted by orienting to a position which varies according to a patient's breathing, of a subject on which treatment is to be carried. The respiration gating system includes: a breathing respirator for allowing the patient's respiration amount to be measured; external markers to be respectively adhered to triangulation points outside a human body of the surrounding region of the subject of the patient on which treatment is to be carried out; an image diagnosis device for imaging the region of the subject of the patient on which treatment is to be carried out by photographing the same; and a computer program programmed so as to calculate, as position coordinates, the change in position of the subject on which treatment is to be carried out, according to the respiration amount measured by the computed tomography equipment and the each external marker, through a triangulation method and dual polynomial equations, and to transmit the position coordinates, which changes in real time, to radiation therapy equipment.

Further, the image diagnosis device may be a computed tomography (CT) device, fluoroscopy or magnetic resonance (MR) imaging device.

Further, according to another aspect of the present invention, there is provided a method for emitting radiation by a respiratory gating system allowing radiation to be emitted by orienting to a position, which varies according to a patient's breathing, of a subject on which treatment is to be carried out. The method includes putting a breathing respirator which transmits a respiration amount on a nasal cavity and a mouth of a patient; adhering external markers to triangulation points outside a human body of the surrounding region of the subject of the patient on which treatment is to be carried out; imaging a position of the subject on which treatment is to be carried out according to a signal of a depth and an amount of respiration by a respiration amount of the patient which is transmitted from the breathing respirator by computed tomography (CT) equipment in real time; measuring the change in position, which is imaged by the external markers, of the subject on which treatment is to be carried out; calculating, as a position coordinate, the change in position of the subject on which treatment is to be carried out using a triangulation method and dual polynomial equations; and transmitting the position coordinates to radiation therapy equipment to emit radiation to the subject on which treatment is to be carried out, whose position varies.

The triangulation equation may estimate the position, which varies, of the subject on which treatment is to be carried out, on an XY coordinate with respect to triangulation positions of external markers and the dual polynomial equations may track a trajectory according to the change in position of the subject on which treatment is to be carried out which is estimated by the triangulation equation and then create an equation using a vector value of the trajectory to calculate the position coordinate.

Collecting of a signal of a depth and an amount of the respiration may include: measuring a physical phenomenon such as a pressure using data acquisition (DAQ); patterning an input signal value using a field programmable gate array (FPGA) on the signal collected in the measuring of a physical phenomenon in an image diagnosis device; and adjusting an on/off time of radiation based on information obtained by patterning the signal value according to movement in the patterning of a signal value.

Advantageous Effects

According to the respiratory gating system for a patient using a natural breathing method during radiation therapy and the method for emitting radiation thereby of the present invention, the accuracy and stability of the entire radiation therapy result may be further increased by tracking, in real time, the movement of an organ, which is the subject on which treatment is to be carried out according to breathing, through a respiratory gating system which uses natural breathing rather than a breathing method through the training of the patient.

Moreover, the radiation may be emitted on a more accurate position, which varies in real time according to a patient's breathing, of the subject on which treatment is to be carried out by measuring a position of the subject on which treatment is to be carried out, through three external markers which are located outside the patient and calculating the change in position of the subject on which treatment is to be carried out, through a triangulation method and dual polynomial equations.

DESCRIPTION OF DRAWINGS

FIG. 1 is a conceptual view illustrating a wearing status of a breathing respirator which configures a respiratory gating system for a patient using a natural breathing method during radiation therapy according to the present invention.

FIG. 2 is a conceptual view illustrating an arrangement of external markers which configure a respiratory gating system for a patient using a natural breathing method during radiation therapy according to the present invention.

FIG. 3 is a conceptual view illustrating change in position of a subject on which treatment is to be carried out according to a respiration amount using a respiratory gating system for a patient using a natural breathing method during radiation therapy according to the present invention.

BEST MODE

Hereinafter, exemplary embodiments of a respiratory gating system for a patient using a natural breathing method during radiation therapy and a method for emitting radiation thereby will be described in detail with reference to drawings. The present invention is not limited to embodiments to be disclosed below, but various forms different from each other may be implemented. However, the embodiments are provided to be completely known to those skilled in the art.

FIG. 1 is a conceptual view illustrating a wearing status of a breathing respirator which configures a respiratory gating system for a patient using a natural breathing method during radiation therapy according to the present invention and FIG. 2 is a conceptual view illustrating an arrangement of external markers which configure a respiratory gating system for a patient using a natural breathing method during radiation therapy according to the present invention.

As illustrated in FIGS. 1 and 2, a respiratory gating system for a patient using a natural breathing method during radiation therapy according to the present invention includes a breathing respirator 1, an image diagnosis device, three external markers 2, and a computer program which calculates position coordinates of a position which varies, of a subject on which treatment is to be carried out, through the above-mentioned components.

The breathing respirator 1 is put on a nasal cavity and a mouth of a subject, of a patient 3, on which treatment is to be carried out and radiation is to be emitted to guide and transmit inhalation and exhalation amounts of the patient 3 during radiation therapy, that is, a respiration amount.

Even though not illustrated, the image diagnosis device including computer images signals of a depth and an amount of respiration which is transmitted through the breathing respirator 1 in real time by photographing the same. Specific examples of the image diagnosis device include a computed tomography (CT) device, fluoroscopy or magnetic resonance (MR) imaging device.

The three external markers 2 are adhered to triangulation points of three places outside the human body in an area surrounding the target region or subject 1a for example on the abdomen and the sides to measure the change in position of the subject on which treatment is to be carried out according to the respiration amount, on an XY coordinate.

The computer program is installed in a computer of an image diagnosis device. The image diagnosis device images the subject 1a of the patient 1 on which treatment is to be carried out by photographing the subject 1a. The computer program drives a program of a triangulation method and dual polynomial equations which measure the position which varies, of the subject 1a on which treatment is to be carried out, by three external markers 2, using the image of the photographed subject on which treatment is to be carried out and calculate the position as position coordinates. Examples of the dual polynomial equations may include linear and quadratic equations, log, and exponent.

Embodiments

Next, a method for emitting radiation by the respiratory gating system for a patient using a natural breathing method during radiation therapy configured as described above will be described.

FIG. 3 is a conceptual view illustrating change in position of a subject on which treatment is to be carried out according to a respiration amount using a respiratory gating system for a patient using a natural breathing method during radiation therapy according to the present invention.

Referring to FIGS. 2 and 3, first, a breathing respirator 2 is worn on a nasal cavity and a mouth of a patient and whenever the patient naturally breathes, a signal of a depth and an amount of respiration is imaged in real time using the image diagnosis device.

Next, in an imaging step, a position, which varies, of the subject 1a on which treatment is to be carried out and radiation is to be emitted is measured with respect to three external markers 3, using the image of the photographed region of the subject 1a of the patient 1 on which treatment is to be carried out.

Next, a trajectory of coordinates on which the subject 1a, which varies, on which treatment is to be carried out is located is tracked by a computer program through the triangulation method and a real-time trajectory equation is created using a vector value of the trajectory through the dual polynomial equations. For example, the position, which varies on the XY coordinate, of the subject on which treatment is to be carried out is measured by three external markers 3 and the positions are connected to be represented by a trajectory. The trajectory is used to obtain an equation which is one of y=ax, y=ax+bx, y=ax+bx+c, y=ax$^2$, y=ax$^2$+bx, y=ax$^2$+bx+c by the dual polynomial equations. Therefore, the change in position of the subject on which treatment is to be carried out according to variables of the respiration amount is mathematized through the equation to be calculated as a position coordinates. In this case, collecting of a signal of the respiration amount includes (a) measuring a physical phenomenon such as a pressure using data acquisition (DAQ), (b) patterning an input signal value using a field programmable gate array (FPGA) on the signal collected in step (a), and (c) adjusting an on/off time of radiation based on information obtained by patterning the signal value according to movement in step (b). As an example of the dual polynomial equations, log or exponent which is described above may be used in addition to the linear and quadratic equations.

Next, the position coordinates which are obtained by tracking the position, of the subject 1a on which treatment is to be carried out, which varies in real time according to a natural breathing amount during the radiation therapy of the subject 1a of the patient on which treatment is to be carried out are transmitted to radiation therapy equipment so that the radiation therapy equipment irradiates radiation onto the subject 1a on which treatment is to be carried out on an accurate position according to the position coordinates which vary.

As compared with a method of controlling a radiation beam to be on/off in a region of the subject, which is a moving target, on which treatment is to be carried out, by receiving breathing phase data of the related art, according to the respiratory gating system of the present invention may more accurately secure the movement of the subject on which treatment is to be carried out which is a target using not only a respiration amount but also a distortion through the triangulation method and the dual polynomial equations. Further, according to the respiratory gating system of the present invention, data of the position coordinate obtained from the patient is created as a respiratory pattern portfolio to be applied in an actual clinical treatment and a position coordinate of the subject (tumor) on which treatment is to be carried out is called in form of a library using inhalation and exhalation amounts, regardless of regular/irregular breathing pattern of the patient to input the position coordinate to the radiation therapy equipment in real time. The radiation therapy equipment which receives the position coordinate starts the image guided radiation therapy (IGRT) and the respiratory gated radiation therapy (RGRT) according to a determined coordinate. In this case, the image guided radiation therapy (IGRT) or the respiratory gated radiation therapy (RGRT) is determined in accordance with a breathing pattern classification of the patient. Therefore, in the case of a simple breathing pattern, a therapy system which is close to the IGRT may be selected.

As described above, the respiratory gating system for a patient using a natural breathing method during radiation therapy according to the present invention and the method for emitting radiation thereby have been described. However, the present invention is not limited to the exemplary embodiments and the drawings disclosed herein. Further, it should be understood that those skilled in the art may modify the present invention in various forms within the scope of the technical spirit of the present invention.

INDUSTRIAL APPLICABILITY

The present invention may be utilized as a respiratory gating system for a patient using a natural breathing method during radiation therapy and a method for emitting radiation thereby which may increase the accuracy and stability of the entire radiation therapy result by tracking, in real time, the movement of an organ, which is the subject on which treatment is to be carried out according to breathing, through a respiratory gating system which uses natural breathing rather than a breathing method through the training of the patient.

Moreover, the present invention may be further utilized as a respiratory gating system for a patient using a natural breathing method during radiation therapy and a method for emitting radiation thereby which may emit the radiation on a more accurate position, which varies according to a patient's breathing, of the subject on which treatment is to be carried out by measuring a position of the subject on which treatment is to be carried out, through three external markers which are located outside the patient and calculating the change in position of the subject on which treatment is to be carried out, through a triangulation method and dual polynomial equations.

The invention claimed is:

1. A respiratory gating system for a patient using a natural breathing method, the system allowing radiation to be emitted by orienting to a position which varies according to a patient's breathing during radiation therapy of a target region of the patient on which treatment is to be carried out, the system comprising:
- a breathing respirator configured to be placed over the patient's nasal cavity and mouth for allowing the patient's respiration amount to be measured;
- a field programmable gate array (FPGA) that receives pressure data from the breathing respirator, determines a depth and amount of respiration, and generates a regular or irregular breathing pattern of the patient;
- external markers to be respectively adhered to triangulation points in an area surrounding the target region;
- an image device for imaging the target region by photographing the target region;
- a non-transitory computer-readable storage media having instructions stored thereon that, when executed by a processor, causes the processor to perform
  (a) triangulating an XY coordinate of the target region with coordinates of the external markers to estimate a position of the target region,
  (b) repeating the triangulation as the patient breathes to determine a trajectory along which the target region is moving, (c) generating a polynomial approximation of the trajectory, and
(d) generating position coordinates of the target region derived from the polynomial approximation; and
radiation therapy equipment that is configured to receive the position coordinates of the target region generated by the computer and adjust an on/off time of radiation based on a classification of the patient's breathing pattern.

2. The system of claim 1, wherein the image device is a computed tomography (CT) device, fluoroscopy or magnetic resonance (MR) imaging device.

3. A method for emitting radiation to a target region of a patient on which treatment is to be carried out by a respiratory gating system allowing radiation to be emitted by orienting to a position, which varies according to a patient's breathing, the method comprising:
   collecting pressure data from the patient using a breathing respirator positioned over a nasal cavity and a mouth of the patient;
   adhering external markers to triangulation points outside the patient's body in an area surrounding the target region;
   imaging a changing position of the target region due to respiration;
   measuring the change in position, based on images of the external markers, of the target region;
   triangulating an XY coordinate of the target region with coordinates of the external markers to estimate a position of the target region, and repeating the triangulation as the patient breathes to determine a trajectory along which the target region is moving;
   generating a polynomial approximation of the trajectory;
   transmitting the position coordinates of the target region, derived from the polynomial approximation, to radiation therapy equipment to emit radiation to the target region so that the radiation therapy equipment can more accurately track the target region as the patient breathes;
   processing the pressure data, using a field programmable gate array (FPGA), to determine a depth and an amount of respiration;
   classifying the patient's breathing pattern as a regular or irregular breathing pattern based on the determined depth and amount of respiration; and
   adjusting an on/off time of radiation based on the patient's breathing pattern classification.

* * * * *